US00PP33871P3

(12) United States Plant Patent
Boches

(10) Patent No.: US PP33,871 P3
(45) Date of Patent: Jan. 18, 2022

(54) BLUEBERRY PLANT NAMED 'FC14-062'

(50) Latin Name: ***Vaccinium corymbosum* hybrid**
Varietal Denomination: FC14-062

(71) Applicant: Fall Creek Farm and Nursery Inc., Lowell, OR (US)

(72) Inventor: Peter Stefan Boches, Hilo, HI (US)

(73) Assignee: FALL CREEK FARM AND NURSERY INC., Lowell, OR (US)

( * ) Notice: Subject to any disclaimer, the term of this patent is extended or adjusted under 35 U.S.C. 154(b) by 0 days.

(21) Appl. No.: 17/166,536

(22) Filed: Feb. 3, 2021

(65) Prior Publication Data

US 2021/0251115 P1 Aug. 12, 2021

Related U.S. Application Data

(60) Provisional application No. 62/995,598, filed on Feb. 6, 2020.

(51) Int. Cl.
*A01H 5/08* (2018.01)
*A01H 6/36* (2018.01)

(52) U.S. Cl.
USPC ..... Plt./157
CPC ..... *A01H 6/368* (2018.05)

(58) Field of Classification Search
USPC ..... Plt./157
See application file for complete search history.

*Primary Examiner* — Susan McCormick Ewoldt
(74) *Attorney, Agent, or Firm* — Panitch Schwarze Belisario & Nadel LLP; Stephany G. Small; Travis W. Bliss

(57) ABSTRACT

The new blueberry plant variety 'FC14-062' is provided. 'FC14-062' is a commercial variety intended for the hand harvest fresh fruit market. The variety is produced from a cross of 'Blue Ribbon' (female parent, patented Jul. 15, 2014) and 'FC10-069' (male parent, unpatented), which can be distinguished by its outstanding features.

7 Drawing Sheets

Latin name of the genus and species:
Genus: *Vaccinium.*
Species: *corymbosum* hybrid.
Variety denomination: The new blueberry plant claimed is of the variety denominated 'FC14-062'.

STATEMENT REGARDING FEDERALLY-SPONSORED RESEARCH AND DEVELOPMENT

None.

BACKGROUND OF THE INVENTION

The present invention relates to the discovery of a new and distinct cultivar of northern highbush blueberry (*Vaccinium corymbosum* L. hybrid) plant, referred to as 'FC14-062', as herein described and illustrated. The new blueberry plant variety 'FC14-062' is a commercial variety intended for the fresh fruit market. The variety has high plant vigor, with an upright growth habit, and produces large fruit with excellent storability. 'FC14-062' was selected for its above average fruit quality and superior environmental adaptability compared to other early-mid-season varieties.

'FC14-062' differs from the female parent 'Blue Ribbon' in that 'FC14-062' has an upright plant shape and 'Blue Ribbon' has a sprawling plant shape. 'FC14-062' differs from the male parent 'FC10-069' in that it produces larger fruit with a better balance of leaves to fruit.

Pedigree and History: The new blueberry plant originated from a cross of 'Blue Ribbon' (female parent, U.S. Plant Pat. No. 24,636 patented Jul. 15, 2014) and 'FC10-069' (male parent, unpatented) made in Lowell, Oreg., USA in 2011.

The new blueberry variety 'FC14-062' was initially propagated in Lowell, Oreg., USA in 2011 and planted in the Spring of 2012. 'FC14-062' has been found to undergo asexual propagation in Lowell, Oreg. by a number of routes, such as in vitro propagation. Asexual propagation techniques in Lowell, Oreg., such as in vitro propagation, have shown that the characteristics of the new variety are homogenous, stable, and strictly transmissible by such asexual propagation from one generation to another. Accordingly, the new variety undergoes asexual propagation in a true-to-type manner.

'FC14-062' was selected for its superior fruit quality and plant performance. 'FC14-062' is a vigorous, precocious plant with concentrated fruit ripening and high yields competitive with other varieties in the same ripening season. The fruit is large with excellent storability to 45 days and beyond.

SUMMARY OF THE INVENTION

The new blueberry plant variety 'FC14-062' has not been observed under all possible environmental conditions. The phenotype may vary somewhat with variations in environment and cultural practices such as temperature and light intensity without, however, any variance in genotype.

'FC14-062' is distinguished by its vigorous, strong growth habit and fruit quality. The following characteristics of the new cultivar have been repeatedly observed and are determined to be the unique characteristics of the new blueberry plant variety 'FC14-062':

1) Vigorous, strong plant growth with exceptional precocity
2) Early-mid season, concentrated ripening 3) Large fruit size with firm fruit texture
4) Very good, long-term cold storage performance

BRIEF DESCRIPTION OF THE DRAWINGS

The accompanying photographic illustration shows typical specimens in full color of the foliage and fruit of the new variety 'FC14-062.' The colors are as nearly true as is reasonably possible in a color representation of this type.

Figure 1:
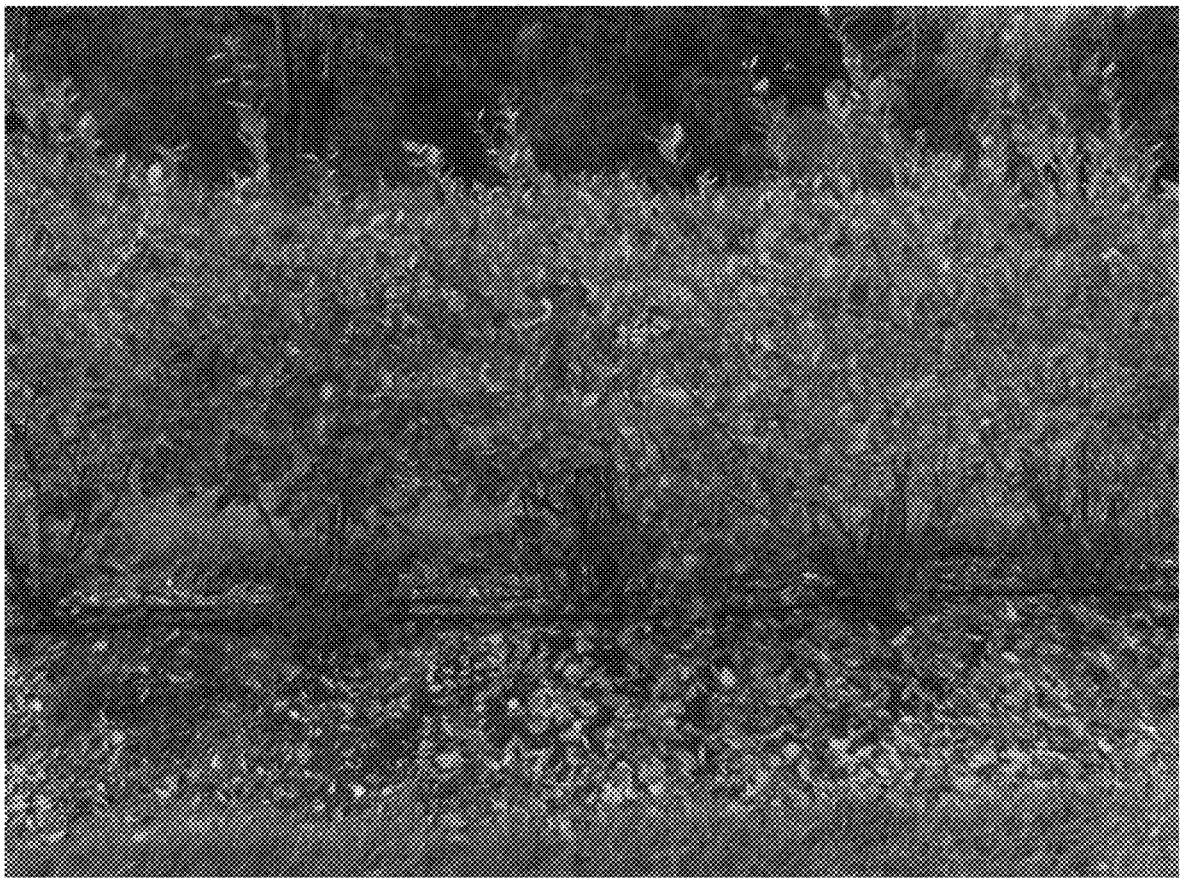
FIG. 1 is a photograph of the new variety 'FC14-062', demonstrating the plant's leaves and growth habit in the fall. The plants were grown in Lowell, Oreg. and photographed on Nov. 16, 2018.
Figure 2:
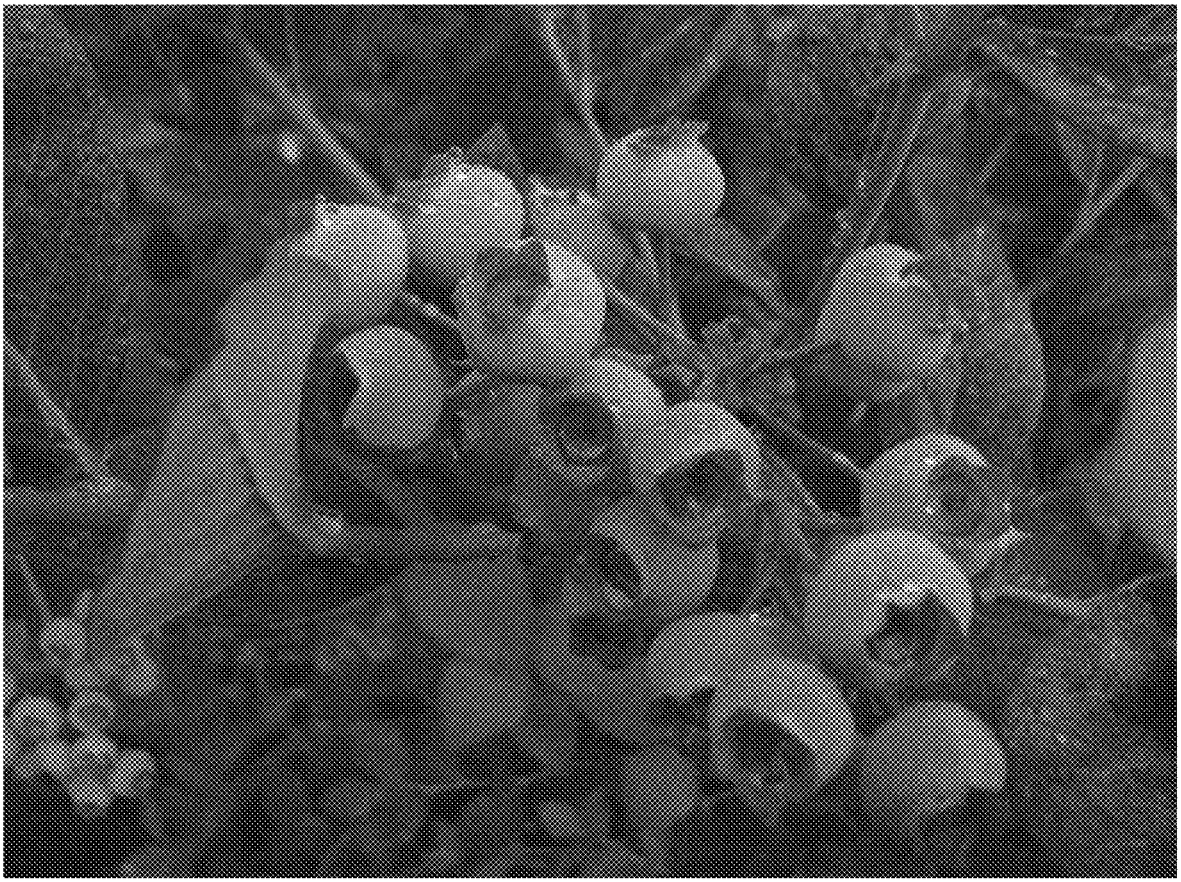
FIG. 2 is a photograph of the fruit cluster of immature fruit of the new variety 'FC14-062' grown in Lowell, Oreg. and photographed on Jun. 18, 2018.
Figure 3:
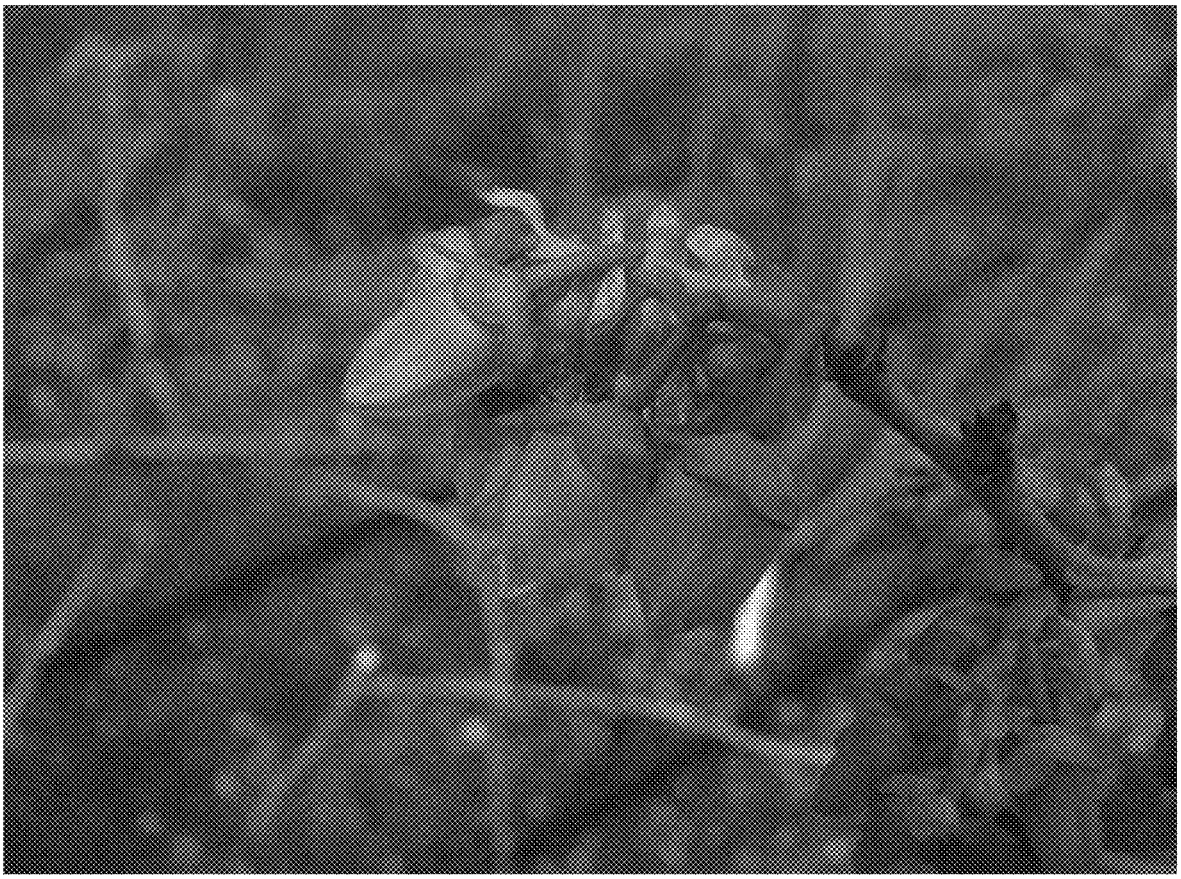
FIG. 3 is a photograph of the flowers of the new variety 'FC14-062' grown in Lowell, Oreg. and photographed on Apr. 18, 2018.
Figure 4:
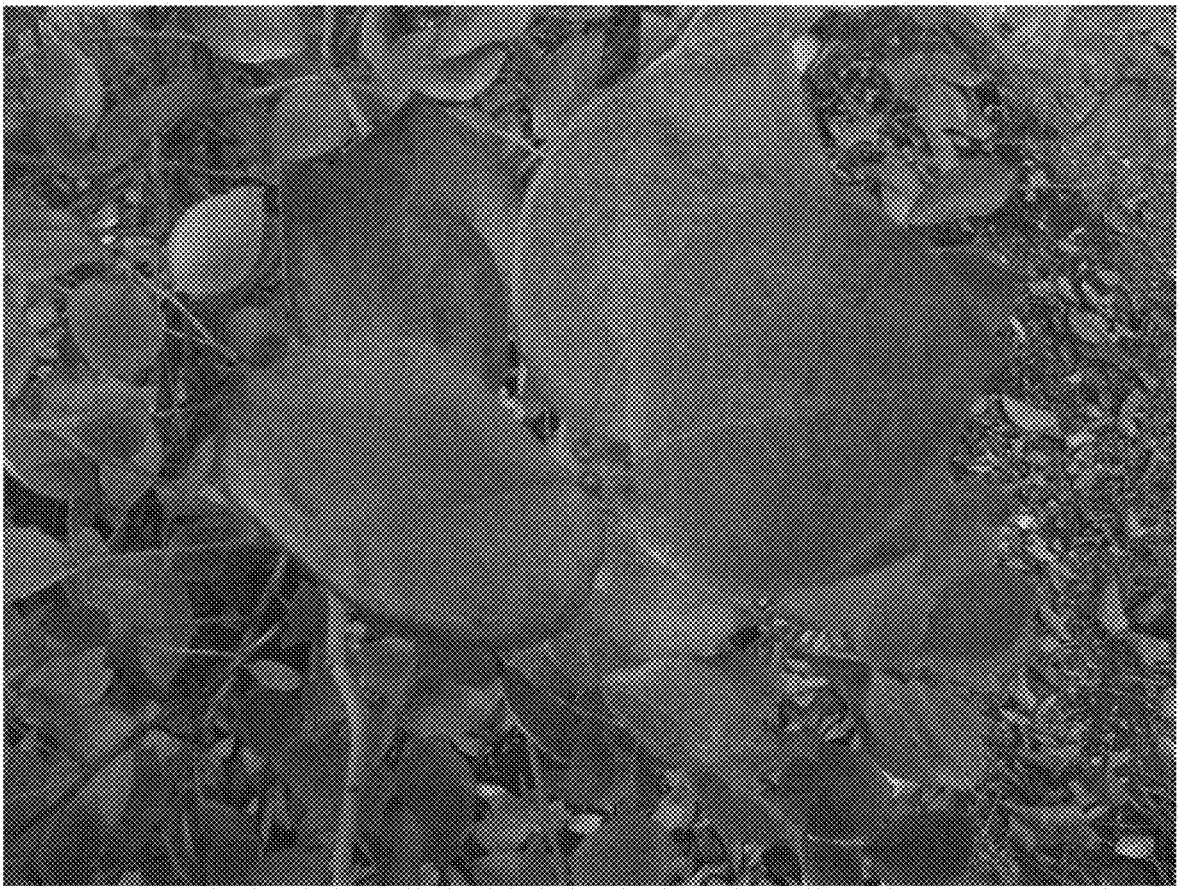
FIG. 4 is a photograph of the fall foliage of the new variety 'FC14-062' grown in Lowell, Oreg. and photographed on Nov. 16, 2018.
Figure 5:
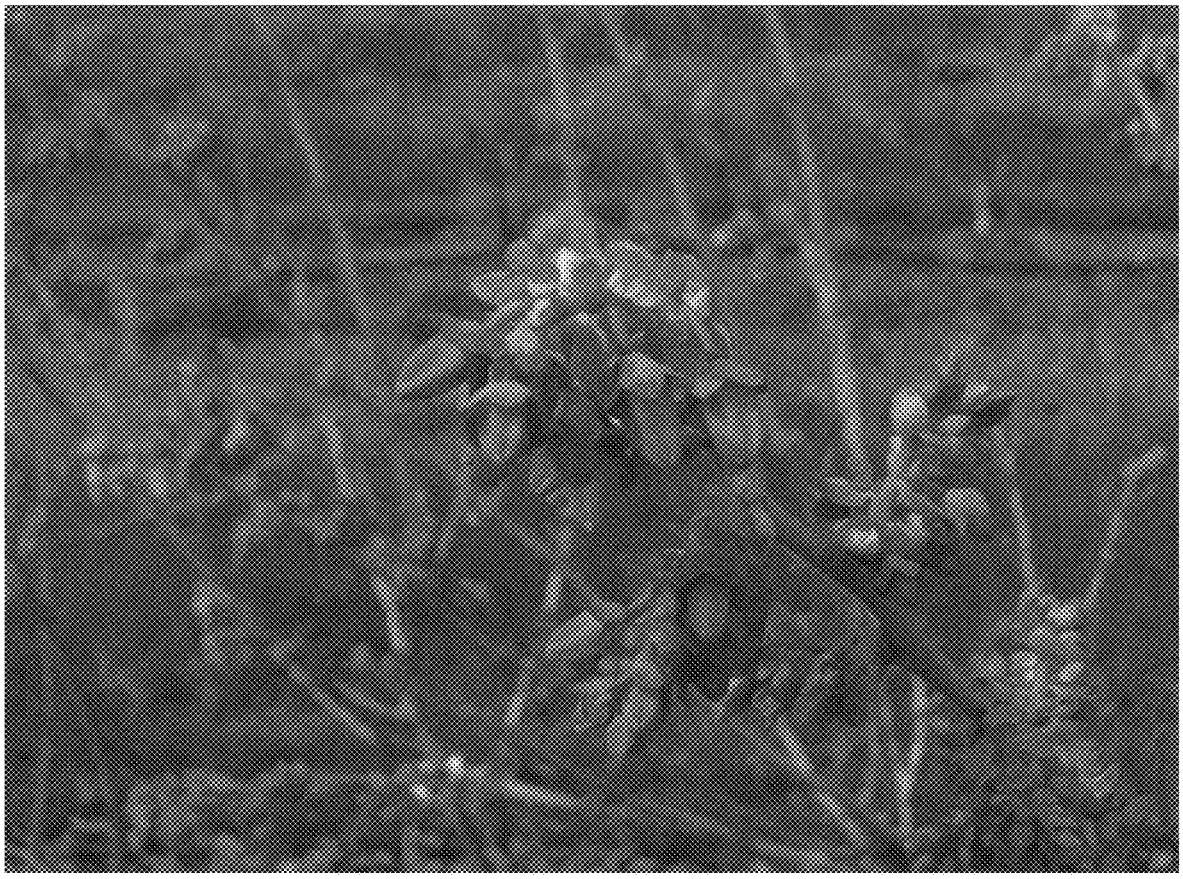
FIG. 5 is a photograph of early buds on the new variety 'FC14-062' grown in Lowell, Oreg. and photographed on Apr. 18, 2018.
Figure 6:
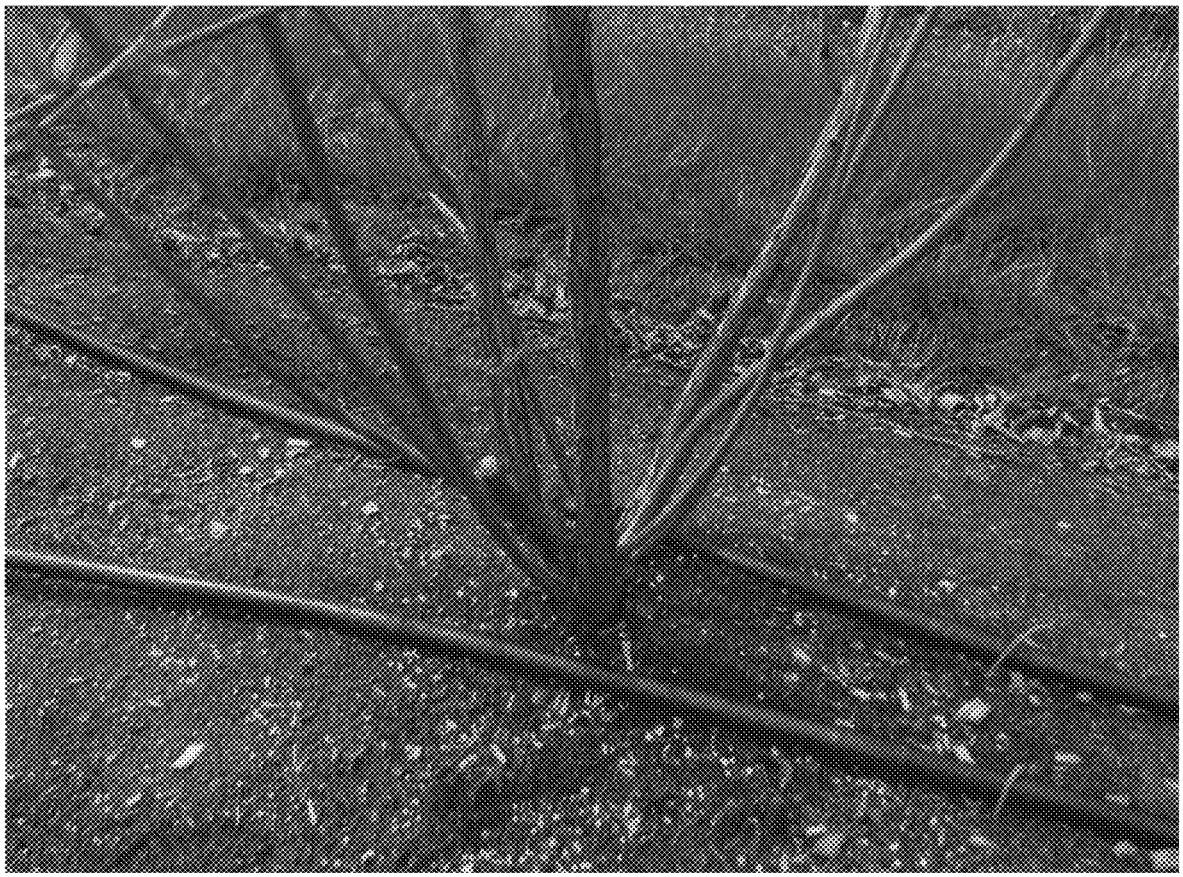
FIG. 6 is a photograph of one-year old canes on the new variety 'FC14-062' grown in Lowell, Oreg. and photographed on Apr. 18, 2018.
Figure 7:
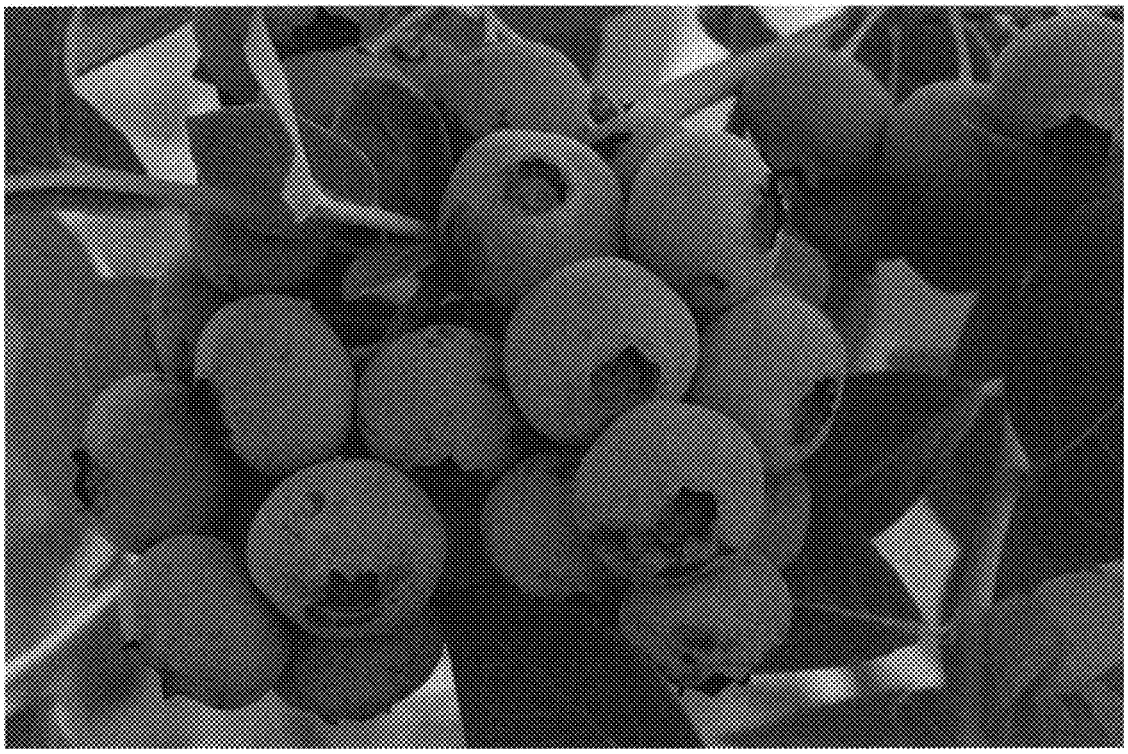
FIG. 7 is a photograph of the mature fruit of the new variety 'FC14-062' grown in Lowell, Oreg. and photographed on Jul. 19, 2017.

The colors in the photographs are as close as possible with the photographic and printing technology utilized. The color values cited in the detailed botanical description accurately describe the colors of the new blueberry.

DETAILED BOTANICAL DESCRIPTION

The following detailed description sets forth the distinctive characteristics of 'FC14-062'. The data which defines these characteristics was collected from asexual reproductions of the original selection. Dimensions, sizes, colors, and other characteristics are approximations and averages set forth as accurately as possible. The plant history was taken on plants approximately 3 to 4 years of age, and the descriptions relate to plants grown in the field located at 39252 Jasper-Lowell Road, Lowell, Oreg., USA. Descriptions of fruit characteristics were made on fruit grown at the field described above. Color designations are from "The Pantone Book of Color" (by Leatrice Eiseman and Lawrence Herbery, Harry N. Abrams, Inc., Publishers, New York 1990). Where the Pantone color designations differ from the colors of the photographs, the Pantone colors are accurate.

Classification:

*a. Family.*—Ericaceae.
*b. Genus.*—*Vaccinium.*
*c. Species.*—*corymbosum* hybrid.
*d. Common name.*—Northern Highbush Blueberry.

Parentage: Female Parent 'Blue Ribbon' (U.S. Plant Pat. No. 24,636 patented Jul. 15, 2014). Male Parent 'FC10-069' (unpatented).

Market class: Commercial production of fresh fruit, but suitable for process market.

PLANT

General:

*a. Parentage.*—Female Parent — 'Blue Ribbon' (U.S. Plant Pat. No. 24,636 patent Jul. 15, 2014). Male Parent — 'FC10-069' (unpatented).
*b. Plant height.*—137.668 cm.
*c. Plant width.*—172.212 cm.
*d. Growth habit.*—Upright.
*e. Amount of growth in a season* (*i.e., plant vigor*).—High.
*f. Productivity.*—High.
*g. Cold hardiness.*—Good.
*h. Chilling requirement.*—Estimated minimum of 800-1000.
*i. Leafing.*—High.
*j. Twigginess.*—Somewhat twiggy.
*k. Resistance/susceptibility to root rot* (*Phytopthora cinnamomii*).—Not overly susceptible.
*l. Resistance/susceptibility to stem blight* (*Botryosphaeria* sp.).—Not overly susceptible.
*m. Resistance/susceptibility to Phomopsis twig blight* (*Phomopsis vaccinii*).—Not overly susceptible.
*n. Resistance/susceptibility to Botrytis* (*Botrytis cinerea*).—Not overly susceptible.
*o. Resistance/susceptibility to leaf spot* (*Septoria* spp.).—Not overly susceptible.
*p. Resistance/susceptibility to leaf rust* (*Naohidemyces vaccinii*).—Not overly susceptible.
*q. Resistance/susceptibility to bud mites* (*Acalatus vaccinii*).—Not overly susceptible.

STEM

General:

*a. Suckering tendency.*—Low.
*b. Mature cane color.*—Pantone color 14-10114 (Gravel).
*c. Mature cane length.*—Average 142.758 cm.
*d. Mature cane width.*—Average 16.810 mm.
*e. Bark texture.*—Rough.
*f. Fall color on new shoots.*—Pantone color 19-1762 (Crimson).
*g. Surface texture of new wood.*—Smooth.
*h. Internode length on strong, new shoots.*—26.466 mm.
*i. Average number of buds per fruiting lateral.*—Average 7.2.

FOLIAGE

General:

*a. Time of beginning of leaf bud burst.*—Mid April in Lowell, Oreg., Early April.
*b. Leaf color* (*top side*).—Pantone color 19-0323 (Chive).
*c. Leaf color* (*under side*).—Pantone color 16-0421 (Sage).
*d. Leaf arrangement.*—Alternate and Spirally: dextrose.
*e. Leaf shape.*—Broadly Elliptic.
*f. Leaf margins.*—Entire.
*g. Undulation of margin.*—None.

*h. Leaf venation*.—Anastomosing.
*i. Leaf apices*.—Slightly Acuminate.
*j. Leaf bases*.—Obtuse.
*k. Leaf length*.—68.212 mm.
*l. Leaf width*.—40.708 mm.
*m. Leaf length/width ratio*.—1.67.
*n. Leaf nectarines*.—Absent.
*o. Pubescence of upper side*.—Absent.
*p. Pubescence of lower side*.—Absent.
*q. Cross sectional profile*.—Slightly Revolute.
*r. Longitudinal profile*.—Flat.
*s. Attitude*.—Porrect.
*t. Fall foliage leaf color* (*top side*).—Pantone color 19-1762 (Crimson).

Petioles:
*a. Length*.—3.628 mm.
*b. Width*.—Average 1.678 mm.
*c. Color*.—Pantone color 12-0418 (Hay).
*d. Petiole surface texture*.—Smooth.

FLOWERS

General:
*a. Time of beginning of flowering*.—Averaging mid to late April in Lowell, Oreg.
*b. Time of* 50% *anthesis*.—Averaging early May in Lowell, Oreg.
*c. Flower shape*.—Urceolate.
*d. Flower bud density*.—Medium.
*e. Flower fragrance*.—None.
*f. Immature flower color*.—Pantone color 15-1922 (Geranium Pink).
*g. Self-compatibility*.—Good. Approximately 72% of self-pollinated flowers set fruit in 2019.

Corolla:
*a. Color*.—Pantone color 11-0603 (Pastel Parchment).
*b. Length*.—9.322 mm.
*c. Width*.—8.25 mm.
*d. Aperture width*.—4.444 mm.
*e. Anthocyanin coloration of corolla*.—Low-None.
*f. Corolla ridges*.—Present.
*g. Protrusion of stigma*.—0.0734 mm below the corolla.

Inflorescence:
*a. Length*.—37.62 mm.
*b. Diameter*.—39.154 mm.
*c. Length of peduncle*.—19.224 mm.
*d. Surface texture of peduncle*.—Smooth.
*e. Color of peduncle*.—Pantone color 17-1633 (Holly berry).
*f. Length of pedicel*.—8.902 mm.
*g. Surface texture of pedicel*.—Smooth.
*h. Color of pedicel*.—Pantone color 17-1633 (Holly berry).
*i. Number of flowers per cluster*.—7.4.
*j. Flower cluster density*.—Medium.

Calyx (with sepals):
*a. Diameter*.—8.488 mm.
*b. Color* (*sepals*).—Pantone color 12-0426 (Mellow Green).

Stamen:
*a. Length*.—6.46 mm.
*b. Number per flower*.—10 stamen per flower.
*c. Filament color*.—Pantone color 12-0524 (Citron).

Pistil:
*a. Length*.—9.63 mm.
*b. Ovary color* (*exterior*).—Pantone color 18-0322 (Cypress).
*c. Style length*.—8.74 mm.

Anther:
*a. Length*.—4.716 mm.
*b. Number*.—2 per filament.
*c. Color*.—Pantone color 16-1342 (Buckskin).

Pollen:
*a. Abundance*.—Moderate.
*b. Color*.—Pantone color 12-0817 (Cornhusk).

FRUIT

General:
*a. Time of fruit ripening*.—Averaging July 12$^{th}$ in Lowell, Oreg.
*b. Time of* 50% *maturity*.—Approximately July 12$^{th}$ in Lowell, Oreg.
*c. Fruit development period*.—Averaging 72 days in Lowell, Oreg.
*d. Mean harvest date*.—Averaging July 16$^{th}$.
*e. Mean date last pick*.—Averaging August 1$^{st}$.
*f. Cluster density*.—Medium-high.
*g. Berries per cluster*.—7.6 berries per cluster.
*h. Unripe fruit color*.—Pantone color 15-0543 (Apple Green).
*i. Ripe berry color*.—Pantone color 16-3919 (Purple Cloud).
*j. Berry skin color after polishing*.—Pantone Color 19-4104 (Ebony).
*k. Berry surface wax abundance*.—Medium.
*l. Berry flesh color*.—Pantone color 11-0304 (Water Lily).
*m. Berry weight*.—Average 2.85 g.
*n. Berry height from calyx to scar*.—13.519 mm.
*o. Berry diameter*.—18.755 mm.
*p. Calyx aperture*.—Average 7.147 mm.
*q. Calyx depth*.—Average 1.075 mm.
*r. Pedicel length*.—Average 10.376 mm.
*s. Pedicel surface texture*.—Smooth.
*t. Berry detachment force*.—Medium-not difficult to pick, no scar tears.
*u. Berry shape*.—Oblate.
*v. Fruit stem scar*.—Small-medium, dry.
*w. Sweetness when ripe*.—Medium.
*x. Firmness when ripe*.—Firm.
*y. Acidity when ripe*.—Medium.
*z. Storage quality*.—Very Good at 42 days normal cold storage at +/−1 C.

SEED

General:
*a. Seed abundance in fruit*.—Medium.
*b. Seed color*.—Pantone color 17-1134 (Brown Sugar).
*c. Seed dry weight*.—0.267 mg. per seed.
*d. Seed length*.—Average 1.5 mm.

COMPARISON BETWEEN PARENTAL AND COMMERCIAL CULTIVARS

TABLE 1

| Denomination of similar variety | Characteristic for comparison | State of expression of similar variety | State of expression of candidate variety 'FC14-062' |
|---|---|---|---|
| 'Draper' (U.S. Plant Pat. No. 15,103) | Vigor | Medium | High |
| 'Draper' (U.S. Plant Pat. No. 15,103) | Storability | Good | Excellent |
| 'Blue Ribbon' (U.S. Plant Pat. No. 24,636) | Yield | 7.2 lbs/plants (3 yrs old) | 9.7 lbs/plants (3 yrs old) |

TABLE 1-continued

| Denomination of similar variety | Characteristic for comparison | State of expression of similar variety | State of expression of candidate variety 'FC14-062' |
|---|---|---|---|
| 'Blue Ribbon' (U.S. Plant Pat. No. 24,636) | Growth Habit | Sprawling | Upright |
| 'FC10-069' | Fruit size | Medium | Large |

The invention claimed is:

1. A new and distinct variety of blueberry plant named 'FC14-062', substantially as illustrated and described herein.

* * * * *